(12) United States Patent
Deubell (10) Patent No.: US 12,160,802 B1
(45) Date of Patent: Dec. 3, 2024

(54) HEALTH EMERGENCY DETECTION, VERIFICATION, ALERT, PATIENT DECISION AND CARE MANAGEMENT SYSTEM

(71) Applicant: Robert M. Deubell, Loveland, OH (US)

(72) Inventor: Robert M. Deubell, Loveland, OH (US)

( * ) Notice: Subject to any disclaimer, the term of this patent is extended or adjusted under 35 U.S.C. 154(b) by 340 days.

(21) Appl. No.: 17/805,538

(22) Filed: Jun. 6, 2022

Related U.S. Application Data (60) Provisional application No. 63/197,177, filed on Jun. 4, 2021.

(51) Int. Cl.
| | |
|---|---|
| *H04W 4/029* | (2018.01) |
| *G06F 21/32* | (2013.01) |
| *G06F 21/62* | (2013.01) |
| *G16H 10/60* | (2018.01) |
| *G16H 40/20* | (2018.01) |
| *H04W 4/021* | (2018.01) |
| *H04W 4/12* | (2009.01) |
| *H04W 4/14* | (2009.01) |
| *H04W 4/90* | (2018.01) |
| *H04W 76/50* | (2018.01) |

(52) U.S. Cl.
CPC .............. *H04W 4/12* (2013.01); *G06F 21/32* (2013.01); *G06F 21/6245* (2013.01); *G16H 10/60* (2018.01); *G16H 40/20* (2018.01); *H04W 4/021* (2013.01); *H04W 4/90* (2018.02); *H04W 76/50* (2018.02); *G06F 2221/2141* (2013.01)

(58) Field of Classification Search
None
See application file for complete search history.

(56) References Cited

U.S. PATENT DOCUMENTS

| | | | | |
|---|---|---|---|---|
| 7,076,235 | B2 * | 7/2006 | Esque | H04W 76/50 |
| | | | | 455/404.1 |
| 7,212,111 | B2 | 5/2007 | Tupler et al. | |
| 8,396,447 | B2 * | 3/2013 | Reich | H04W 4/90 |
| | | | | 455/412.2 |
| 9,717,101 | B1 * | 7/2017 | Burnham | G16H 80/00 |
| 2007/0218895 | A1 | 9/2007 | Saito et al. | |

(Continued)

*Primary Examiner* — Kenneth B Wells
(74) *Attorney, Agent, or Firm* — Wood Herron & Evans LLP (57) ABSTRACT

Medical emergency detection, decision-making, and support are triggered based on location of the user, and protective health documents and other information supporting the user's desired health outcomes are notified and delivered for health care use. When the user's entry into a patient care facility is detected via geofencing or another method such as beacons, and an emergency state is auto detected and/or user declared, alert notifications are triggered. The user's emergency contact information, medical history and other relevant information may be shared with emergency care personnel. Also, the user's emergency contacts and others in the user's care circle may be notified and provided instant online access to the user's protective health documents and other content provided by the user. The access to content to entities and individuals can be based on permission rights the user has predetermined.

22 Claims, 4 Drawing Sheets

(56) References Cited

U.S. PATENT DOCUMENTS

| | | | |
|---|---|---|---|
| 2012/0282887 A1* | 11/2012 | Khoo | H04L 12/1895 |
| | | | 455/404.2 |
| 2014/0279807 A1* | 9/2014 | Dimitrijevic | G16H 50/20 |
| | | | 706/47 |
| 2021/0183502 A1* | 6/2021 | Silverstein | G16H 40/20 |
| 2021/0287784 A1* | 9/2021 | Mullaney | G16H 10/20 |

* cited by examiner

HEALTH EMERGENCY DETECTION, VERIFICATION, ALERT, PATIENT DECISION AND CARE MANAGEMENT SYSTEM

CORRESPONDING APPLICATIONS

The present invention claims the benefit of and priority to U.S. Provisional Patent Application, Ser. No. 63/197,177 filed Jun. 4, 2021, which is incorporated herein in its entirety.

FIELD OF THE INVENTION

The present invention relates to detecting and managing a health emergency event and supporting delivery of protective health documents and information to emergency care personnel and a patient's care circle contacts.

BACKGROUND OF THE INVENTION

In the event of a traumatic injury or other serious medical emergency such as a heart attack or stroke, an injured patient often enters a hospital emergency room or other patient care facility unable to communicate effectively. In this circumstance, medical personnel must attempt to identify and contact the patient's loved ones and other emergency contacts using limited information. This can be difficult, as the patient's personal identification found in a wallet or purse frequently does not include emergency contact information, and the user's mobile device may be locked. Therefore, emergency contacts may not be quickly identified by busy hospital personnel, as important time sensitive decisions are being made. The patient's medical history such as allergies to certain medications may not be readily available.

The patient's protective health documents such as a healthcare durable power of attorney identifying the patient's healthcare agent, medical wishes and directives, and medical history are usually kept as paper copies somewhere making them difficult to access. For the small percentage of the public that have these documents stored electronically on a personal device they still may not be accessed quickly in a time sensitive emergency.

Additionally, today there is no way to predict which emergency room or healthcare facility a given patient may be taken to when in the custody of emergency medical personnel in the event of a health emergency. Furthermore, the facility providing a patient emergency care is typically where the patient will be admitted for additional care even if that facility is not well equipped to handle the patient's ongoing care, or the patient has attending physicians (e.g., cardiologists) at another facility.

Previous systems have been described for use in notifying of individuals who might need to know that an emergency request has been initiated. More particularly, published U.S. Pat. No. 7,212,111 B2 published May 2007, describes a method in which, subsequent to an emergency call, other individuals are automatically notified with the location of the emergency. However, this service does not provide automatic detection of the emergency and does not have an automated way of sharing critical medical information with emergency personnel. It also fails to provide online access to protective health documents or enable proximity-based advocacy for the patient in the event the patient is out of town without other family members.

Other previous systems have described a method for initiating a period of time from the initiation of a security period to the termination of that period of time before an emergency is declared. More particularly published U.S. Patent Publication No. 20070218895A1 published September 2007 (Abandoned) discloses such a system. This service, however, relies on the user to initiate the start of the timer in the affirmative for this period of time.

Thus, there are significant barriers that arise when a health emergency has happened, and there is an ongoing need for a method and apparatus for quickly identifying the patient and the patient's emergency contacts, notifying said emergency contacts, knowing the patient's medical history and healthcare wishes and medical directives, identifying and finding the patient's Health Care Agent found in an executed healthcare durable power of attorney, and identifying healthcare facility preferences if admission to a hospital is necessary. These barriers pose substantial risks to time sensitive medical decisions and the wishes of the patient.

SUMMARY OF THE INVENTION

In certain example aspects described herein, a computer implemented method for alert notifications is provided. A location identifying technology (e.g., GPS, geofencing, Bluetooth beacons, etc.) determines that a user's mobile computing device, such as a mobile telephone, has entered a healthcare facility such as an emergency room. When the user's device has entered a healthcare facility, the system undertakes specific steps to ensure notice, instructions and information are available.

In one embodiment, detection of a geolocation coinciding with a healthcare facility causes the user's device to provide an alert indicating arrival in an emergency care facility and asking the user whether there is a medical emergency. If a medical emergency is confirmed, or after a predetermined amount of time without a response from the user, an alert notification that the user is at the emergency room including details is sent to emergency contacts and others the user has predetermined to receive such emergency alerts.

To alleviate false positive of detection inside of a hospital or emergency room (e.g., due to the limitations of minimum size and accuracy of geofencing), the system can confirm the emergency by redetermining the user's location at a time interval after the first determination of entering the emergency room geofence. Optionally, the system may use additional redeterminations prior to an alert being triggered.

In certain embodiments, the contents of the notification may facilitate instant online access on mobile devices and computers to documents and information, namely protected health documents which may include the user's healthcare durable power of attorney, healthcare wishes and directives, medical summary, and other documents such as last will and testament, insurance policy information, and other information the user may choose to provide. The type of healthcare documents made available to each user can be configured.

In certain other embodiments, users predefine their preferred healthcare facilities and medical personnel preferences, and/or facilities or professionals they wish to exclude, in the event they are admitted to a hospital after emergency room treatment. These preferences may include identification of persons to be admitted to a patient's room, the patient's religious practices, and other preferences. As an example, a user with a history of heart disease may prefer a hospital where the patient's current cardiologist has admitting privileges. In another example, the user's health insurance provider may have designated the closest hospital as "out of network" and therefore the user may wish to exclude that hospital.

In certain other embodiments, users can document and define their wishes concerning life support, organ donation, define emergency contacts, care circle contacts, and healthcare agent(s) are provided herein, and translates such wishes determined through online questions into documents and other information that can be printed or viewed electronically by others. The user can define permission level access to documents and information based on the user type or by the user. When an emergency health event has been identified, the contacts and healthcare agent can post updates about the user to said care circle and other advocates.

In certain other embodiments, members or groups who have enrolled in the system to provide patient advocacy who are within a defined proximity boundary of the user's identified location may be sent alert notifications requesting their assistance. These members or groups are separate from the predefined contacts of the user. These alert notifications may include the name of the user who is having a health emergency and profile information, location of the emergency room or healthcare facility the user is located in, the type and disposition of the assistance request if available, and other information. In certain other example aspects, the embodiments provide methods for said members or groups to accept a request for assistance. When a request has been accepted, the status of the request is changed. When said acceptance has occurred the permission level for the accepting member may change, providing access to other documents and other information the user or healthcare agent has chosen to share with responding members or groups.

These and other aspects, features and advantages of the example embodiments will become apparent to those having ordinary skill in the art upon consideration of the following detailed description of the illustrated example embodiments.

The above and other objects and advantages of the present invention shall be made apparent from the accompanying drawings and the description thereof.

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE INVENTION

Figure 1:
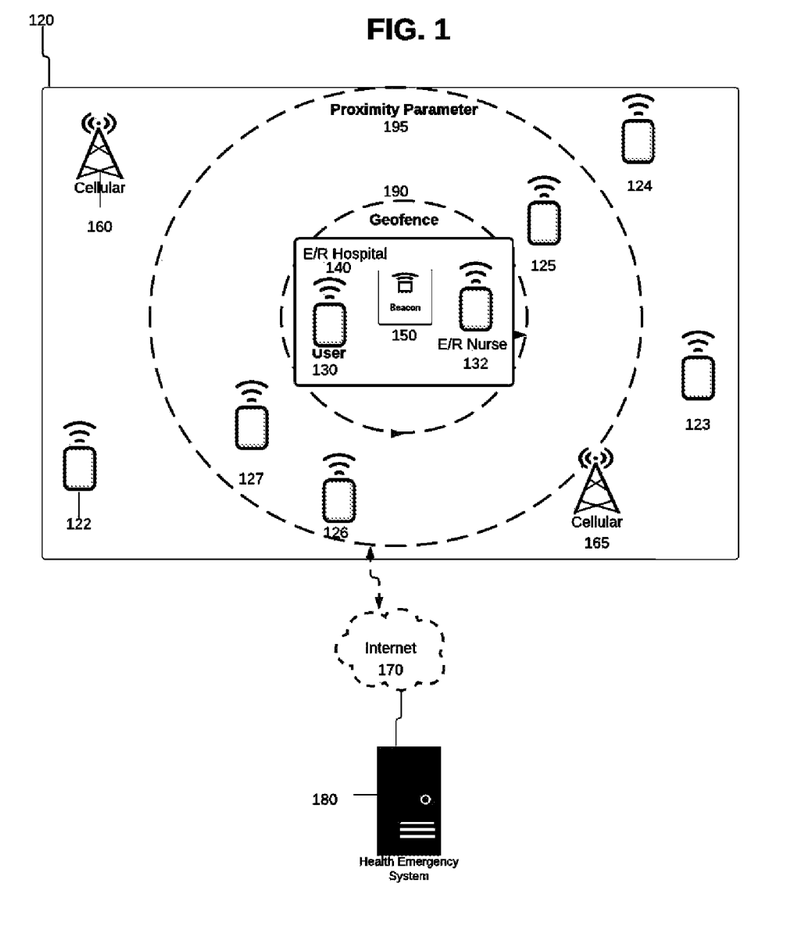
FIG. 1 is a diagram depicting a hospital/emergency room geofence boundary based on proximity in relation to the primary user and other geofence boundaries based on proximity of the hospital/emergency room to other members.

FIG. 1 depicts a block diagram of a wireless communications system 120. As disclosed herein, an emergency alert geofence management and content distribution system 180 obtains location data for hospitals and other emergency care facilities 140, such as latitude and longitude coordinates. The system then determines with the authorization of the user, the location of the user's mobile computing device 130 relative to hospitals and other emergency care facilities and alerts the user when they have entered the geofence 190 of such emergency care location. To reduce false positives that may exist due to the limitations of accuracy in determining if a user's mobile device has entered an emergency care geofence 190 the system has the ability, once the user entered the geofence, to redetermine the user's location again after a time interval before issuing an alert to the user. For example, when the user's device has entered the geofence for the first time, the system waits ten minutes and checks the user's location again before issuing the alert. This minimizes the false positive of determining a user is in an emergency room when the user is merely driving past a hospital. In order to use the system as described herein, the user may have to install the system application on the user device and/or specify settings on the user device. In some embodiments the user's location relative to an emergency room or hospital is determined via said emergency room or hospital's Bluetooth beacons.

Figure 3:
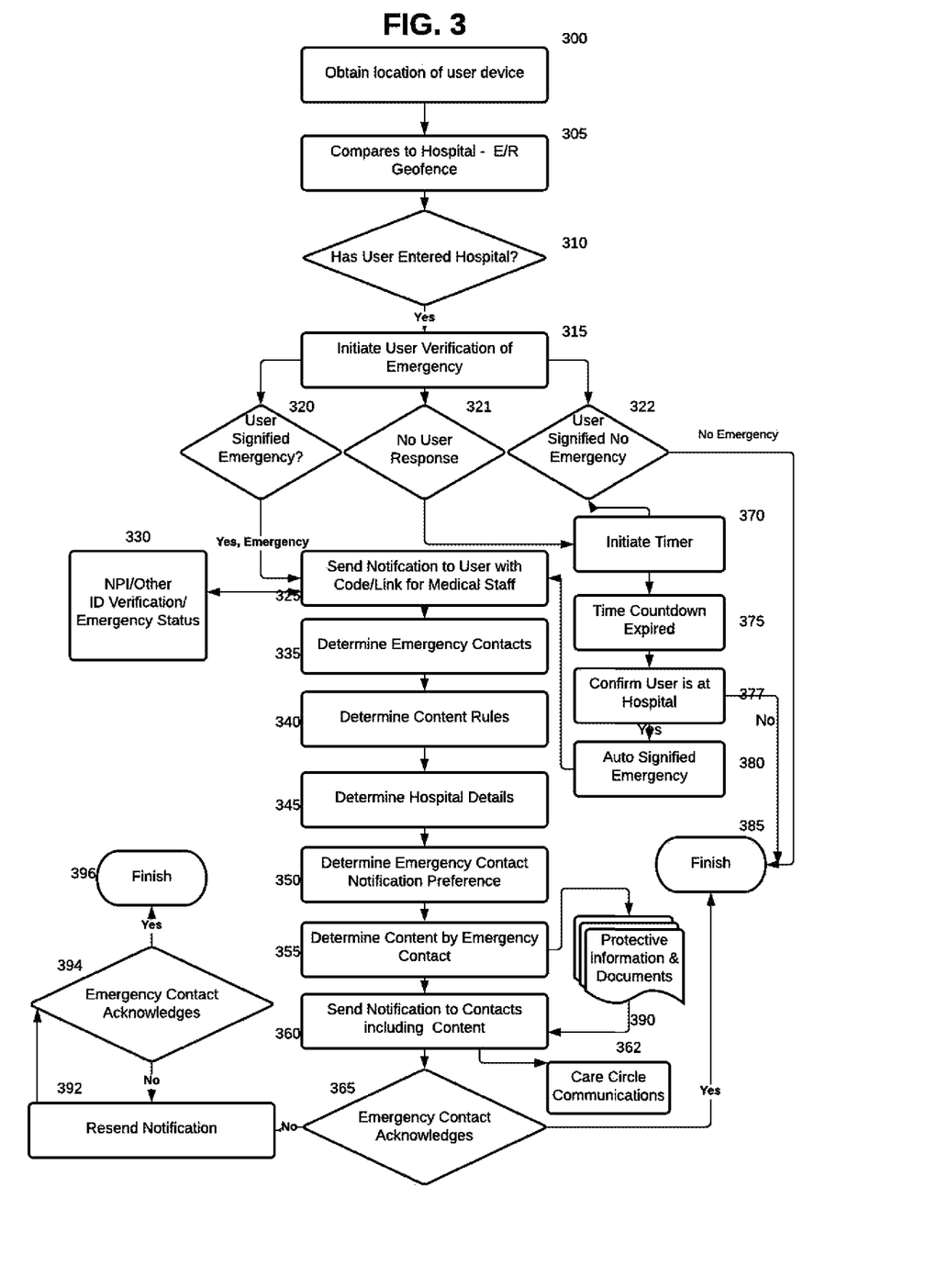
FIG. 3 is a block flow diagram depicting a method of identifying a health emergency and alerting emergency contacts and providing protective health documents.
Figure 4:
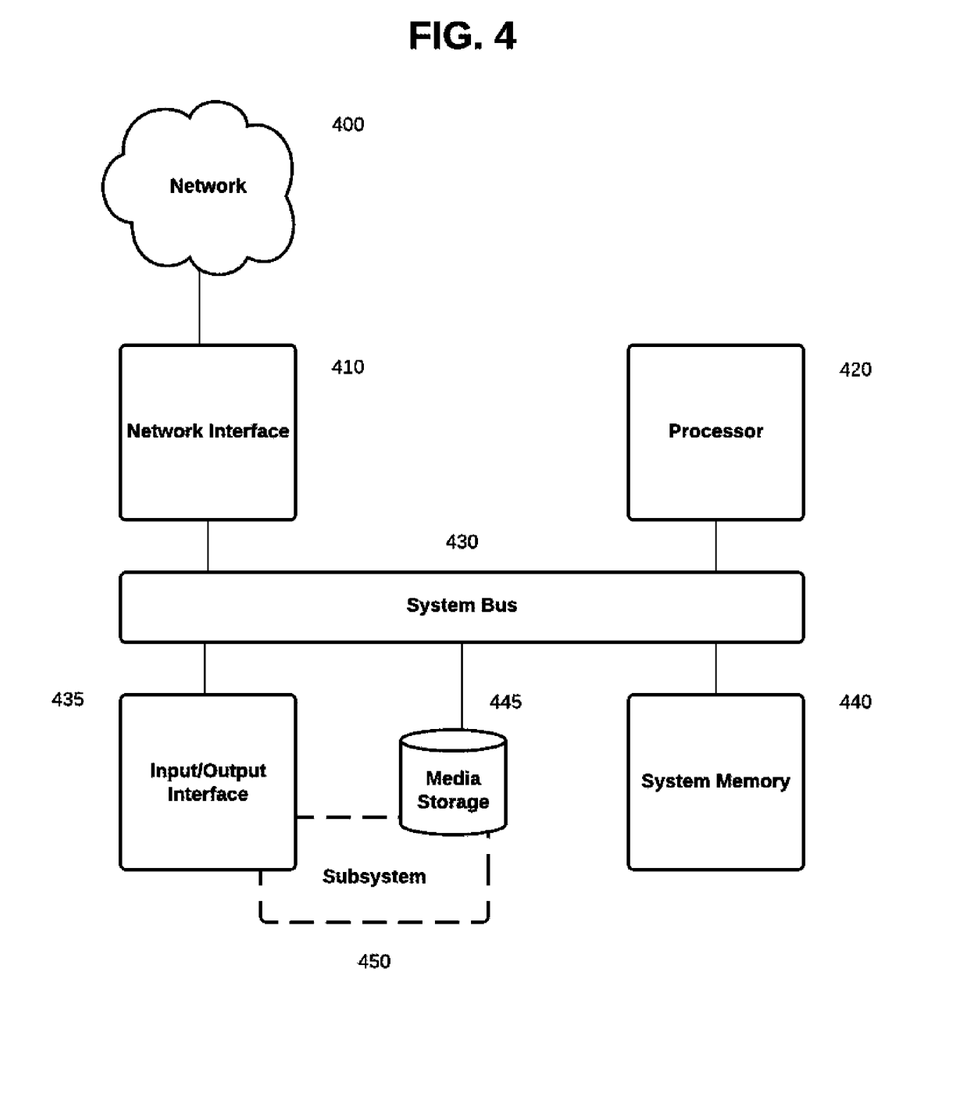
FIG. 4 is a block diagram depicting a computing machine and a subsystem, in accordance with certain example embodiments.

FIG. 3 depicts a simplified flow diagram of a process for identifying an emergency based on the location of the user 300 and contacting and delivering 360 protective health information, to emergency contacts 355 and others in the user's care circle. In certain example embodiments, when the user has not responded 321 to verification of an emergency 315, the alert notification is not sent upon the first instance of determining that the user's device has entered the hospital geofence 310. The system after determining the user's device has entered the emergency room 310 stores the instance details of this first identification of the user's entry into the location, including user ID, location details, and time stamp, and then initiates a timer 370. When said timer's predetermined time value is reached 375 the system then recalculates the user's location to determine if the user's mobile device continues to be within the emergency room location. If the user has been redetermined to be within the facility again then the alert notification is sent to the user's mobile device 325.

Figure 2:
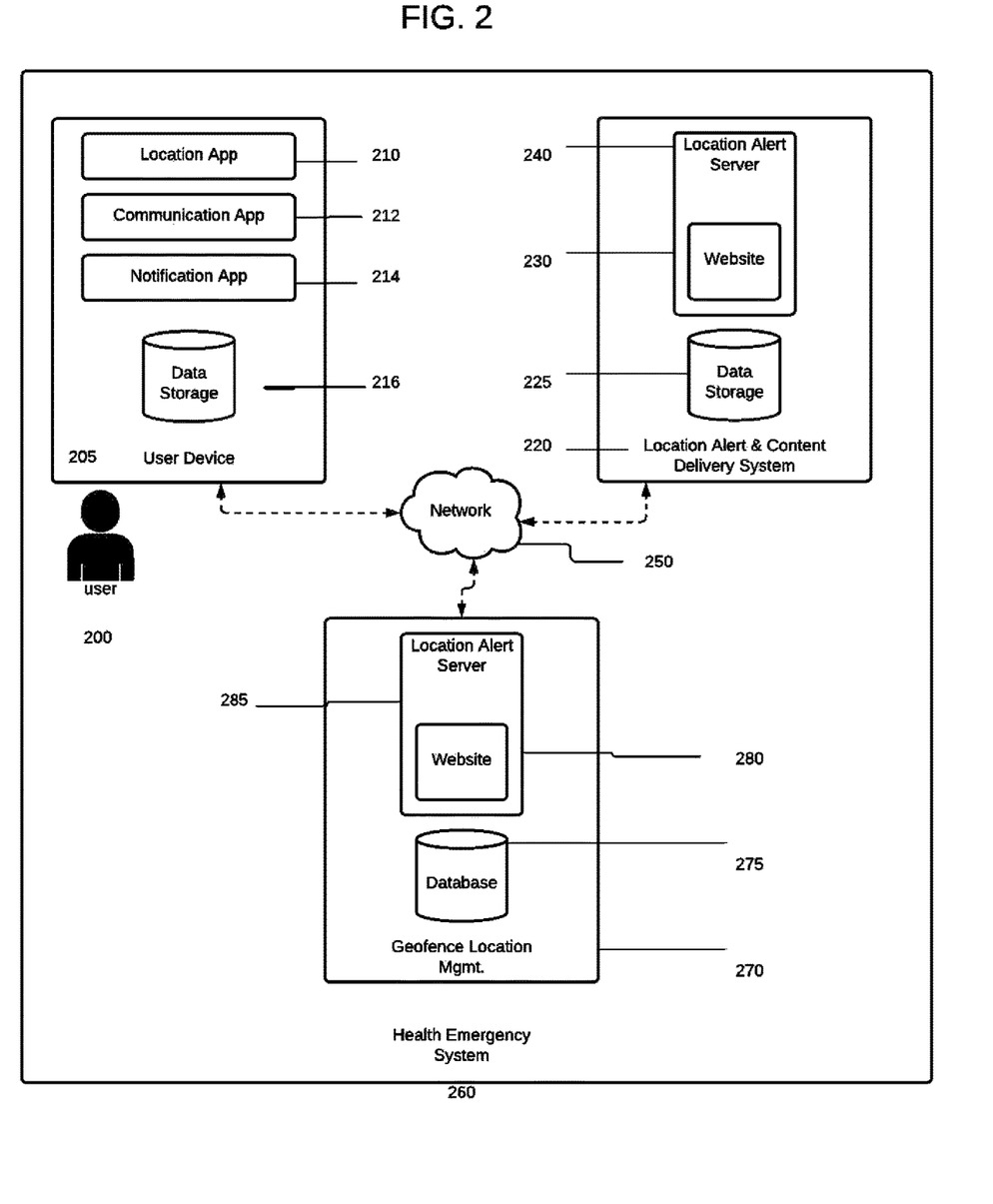
FIG. 2 is a block diagram depicting a system for geofence-based alerts and content delivery in accordance with certain example embodiments.

FIG. 2 depicts a block diagram of the Health Emergency system 260. When preauthorized by the user the system obtains the location information of the user's mobile device 205. The user may have to activate and/or allow the device to monitor the device location continually or continuously for use in determining the entry into an emergency room or hospital facility. Specifically, when preauthorized by the user, the location of the user device is determined such as through a location application 210 on or provided by the phone manufacturer that is associated with a location service. The location of the user can also be determined through any combination of Location Services, Assisted GPS or Bluetooth beacons 150. In certain example embodiments, the system operates as a location-based service that monitors the location of the user's device in relation to an emergency care or hospital facility. For example, a location application on the user's device determines its location and communicates the device location to the system 180. The system receives the location information, such as the latitude and longitude coordinates of the device and monitors the location of such device in relation to the locations of emergency room or hospital facilities 140. In other example embodiments, the system may operate partially or entirely on the user's device 130.

The system stores the location information of hospital and other emergency rooms, such as the latitude and longitude coordinates in a database 275, as well as other information such as address, phone number, and other information. In certain example embodiments the location information of hospital and other emergency care facilities may be hosted and accessed from a third party through an application protocol interface (API) such as an HTTP request.

In an example embodiment, the system utilizing a location application protocol interface (API) or another similar service communicates the emergency room geofence information to the user device 205. The location information may include the latitude and longitude of the emergency room. The user's device then stores the coordinates, for example in the cache of the user's device 216. The system then determines that the user's device enters the facility's geofence or perimeter 270. For example, an application on the user's device, such as the location application, monitors for an entry event into the geofence 190. The user's device then notifies the system of the entrance event. The system notifies the user's device 205 providing an alert notification to the user 200. The system also provides content information included in the alert notification to the user's device.

In the illustrated embodiment, the content accompanying the alert includes a message to the user's mobile device 205 indicating that the system identified the user as being in an emergency room and asking the user if they are OK 315. The message provided to the user's mobile device is made through app services via a notification and may also have a voice alert through Apple's Siri, Google Assistant, or other voice assistant technology. The user's response 320 & 322 to said inquiry is used by the system in determining whether there is a potential emergency and whether an alert will be sent to the user's emergency contacts, and/or other groups and members. The system provides a method whereby the user can respond to this question such as with a button press via the system's mobile application, a verbal response through Siri, Google Assistant, or other voice assistant technology through said system app, or via an instant or text message response. The possible user response options by the user to said question as to whether they are OK is used by the system to infer and catalogue whether the user is having a medical emergency, or if no response 321 such disposition is yet indeterminate by the system. The user's response is used to determine the appropriate course of action. When the user indicates they are OK 322 the system classifies the entry into the emergency care facility as not being an emergency. In this case of non-emergency the system will send a follow up message to the user's device acknowledging but without any further actions. When a user has indicated they are not OK using the methods above then the system sends an alert notification to the contacts the user has designated to receive notifications 360. These contacts may include emergency contacts, the user's care circle, and other groups and members who are within a predetermined radius of the user's device or based on role. The alert notification includes mobile and online access to documents and other information 390 the user has predetermined they would like a member or group to have access to. Examples of said documents and information include the user's healthcare durable power of attorney, medical history, healthcare wishes and directives, last will and testament, insurance, and other information.

In the disclosed embodiment emergency care facility personnel 325 are also alerted through the user's device, indicating that there is important patient information to be shared with them. When the location management system has made such determination of entry into an emergency room 310 a notification is sent to the user's device 325 with a message instructing emergency care facility personnel to view the message. The notification preview includes a brief note to said emergency room personnel and a QR code, website hyperlink, or alphanumeric code with website URL. These various codes or URL's can then be used by said emergency room personnel to access key information by scanning such QR code on the user's device 130 from a medical staff's personal mobile device 132 or via a barcode scanner into an online, internet connected computing device such as an electronic medical records computing system. When within an emergency care facility, the user's information may also be accessed by medical staff using the user's mobile device 130 to perform a biometric match with the user such as face recognition, retinal scan or fingerprint identification. Such information accessed includes key user information such as emergency contacts 122-124, medical history such as allergies to medications, medical conditions and other relevant information. Emergency contacts and others may also be sent the notification with the QR or other code to receive the key medical and other information that they can share with medical personnel. In an example embodiment the notification to the user's mobile device 130 may include a link that when selected navigates to a mobile webpage that then displays the relevant information on the user's mobile device 130. Such information may include the user's emergency contacts, healthcare agent, medical history, wishes and healthcare directives, and protective documents such as a healthcare durable power of attorney. The information may also include the user's predetermined preferences of hospitals and other care facilities to be admitted to in the event the user would require additional care such as ICU admission. These hospital and care facility preferences can be based on the type of medical condition such as traumatic injury or heart attack, and where their preferred physician for such a condition (e.g., Cardiologist) has admitting privileges.

In an example embodiment the system will send proximity based alert notifications when an emergency has been detected to members or groups 125-127 within a predetermined radius 195 of the user's device when preauthorized by the user. The user may or may not have previously known the identity of these members or groups but has enlisted them previously through rules setup in a system. These members or groups have agreed to provide support to users who have had a medical emergency. For example, if the user is travelling and away from family and friends and has had an accident, members who are nearby the hospital may provide onsite advocacy for the user who has had an accident.

In an example embodiment, when the user's device has been determined to be within an emergency care facility or hospital location 310 and there is no response as to whether they are OK or not OK 321 the system starts a timer 370. When the timer reaches a predetermined total time lapsed 375 and the user still has not responded either that they are OK or not OK, the system will recheck the location of the user to determine if they are still at the hospital or other emergency care facility 377. If the user is determined to be in the hospital or emergency care facility the system will classify the user's entry into the emergency care facility location as an emergency 380 and will send the alert notification to the user's phone 325 and predefined contacts and members or groups 360, if they have designated members or groups to receive such notifications.

In certain other example embodiments, a barcode is sent to specified contacts 360 that can be shared with emergency care facility personnel and others, such as a physician, other healthcare professionals that provides the individual with a link that accesses specific online documents and/or information of the user. For example, the user may wish for their Healthcare Agent to share medical history with physicians of the hospital provided through a 2D or other barcode, link or other code.

In the illustrated embodiment the alert notifications include instant online access on mobile devices and computers to certain summary protective information and documents 390, namely protective health documents and digital summary information which may include the user's healthcare durable power of attorney, healthcare wishes and directives, medical summary, allergies, last will and testament, insurance policy information, and other documents the user may choose to provide. The user predefines which documents, and what protective information and documents 390 will be made available to each contact or group. Such information is stored in a database 225 until an emergency has been detected or signified. Example groups who may be provided access to such information include but are not limited to emergency contacts, emergency health workers such as hospital or E/R staff, healthcare agents and alternates, and primary care physician.

In certain other example aspects, the embodiments provide a system and methods enabling individuals the user has invited to their account, aka care circle members, to communicate with each other in a secure system 362 regarding the user's health condition, care and visitation coordination, task management, calendar updates, facility transfer requests and other aspects. In an example embodiment this communication may also include communication with medical staff 325. Also provided in certain aspects is a method for establishing the content, permission rules to access viewable content of the care circle members and other groups and individuals. In an example embodiment the permission rules may include real-time verification of the identity of the medical staff member 330 prior to permitting access to the user's protective information and documents 390. Such substantiation of identification may include verification of the emergency care facility or hospital staff members unique identifier such as their National Provider Identification (NPI) number or other unique identifier through an online database or other verification methods 330.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A computer-implemented method of auto-detection and notification of a medical emergency, comprising:
   determining, by one or more computing devices, a user's mobile computing device has entered a healthcare facility at a location defined by a location identifying technology;
   sending an alert notification to the user's mobile computing device upon determination that the user's mobile computing device is at an emergency room or healthcare facility;
   confirming an emergency event via the user's proactive response or non-response to the alert notification; and
   sending notifications to the user's predetermined contacts identified by the user prior to the emergency event to alert the predetermined contacts that the user is in a healthcare facility,
   wherein sending notifications to the user or the user's predetermined contacts includes sending information to permit access to the user's health information.

2. The computer-implemented method of claim 1, further comprising:
   upon determining the user's mobile computing device has entered a healthcare facility location, initiating a timer; and
   when a specified total time from initiation of the timer has elapsed, redetermining whether the user's mobile computing device remains within the healthcare facility location, and if so, sending the alert to the user's mobile computing device.

3. The computer-implemented method of claim 1,
   wherein the user's proactive response indicates whether the user is or is not having a medical emergency via an application residing on the user's mobile computing device via verbal input, instant messaging or text message response; and
   upon delivery of the alert notification, initiating a timer, and in the event the user does not respond to the alert notification before a specified total time from initiation of the timer has elapsed, the user is deemed non-responsive, and notifications are sent to the user's predetermined contacts.

4. The computer-implemented method of claim 1,
   wherein sending notifications to the user or the user's predetermined contacts further includes sending contact or location information for the healthcare facility.

5. The computer-implemented method of claim 4,
   wherein the information to permit access to the user's health information is visibly presented on the lock screen of the user's device.

6. The computer-implemented method of claim 1,
   wherein the information to permit access to the user's health information comprises one or more of:
   access credentials for the user's Electronic Medical Record,
   access credentials for the user's Electronic Health Record,
   access credentials for the user's Personal Health Record,
   access credentials for the user's Patient Portal,
   user preferences of physicians, hospitals and other care facilities in the event post emergency care is required, and
   a URL link to a webpage that includes the user's emergency contact details or health information.

7. The computer-implemented method of claim 6,
   wherein the information to permit access the user's health information comprises a prompt for a biometric reading comprising one or more of a face ID, retinal match, or fingerprint.

8. The computer-implemented method of claim 6,
   wherein information to permit access to the user's health information comprises a prompt to emergency personnel for a National Provider Identifier (NPI) or another verifying identifier; and
   further comprising using online verification of the verifying identifier prior to granting access to the user's health information.

9. The computer-implemented method of claim 1,
wherein delivery of the alert to the user's mobile computing device is accompanied by a distinctive auditory alarm.

10. The computer-implemented method of claim 7,
wherein the alert comprises a QR code and voiced utterance instructing the use of the QR code; and
wherein the QR code provides the user's emergency contact details and access to health information previously identified by the user to be provided to emergency medical personnel.

11. The computer-implemented method of claim 1,
wherein the delivery of the alert to the user's mobile computing device is accompanied by a voiced utterance.

12. The computer-implemented method of claim 1,
wherein the alert is delivered to the user's mobile computing device via one or more of text message, email, push notification, a message, a code, and a QR code.

13. The computer-implemented method of claim 1, further comprising:
detecting a medical emergency for the user with a wearable device which determines a user's biometric data has exceeded a threshold; and
sending notifications to the user's predetermined contacts identified by the user prior to the emergency event to alert the predetermined contacts that the user is having a medical emergency.

14. The computer-implemented method of claim 1,
wherein the user's proactive response indicates whether the user is or is not having a medical emergency via an application residing on the user's mobile computing device via verbal input, instant messaging or text message response; and
upon delivery of the alert notification, initiating a timer, and in the event the user does not respond to the alert notification before a specified total time from initiation of the timer has elapsed, the user is deemed non-responsive, and notifications are sent to the user's predetermined contacts.

15. The computer-implemented method of claim 1,
wherein the user defines permission levels for access to documents on a per-user or per-user-type basis.

16. The computer-implemented method of claim 15,
wherein the user further defines individuals or groups that may accept requests for assistance and, in response, provide or receive access to documents based upon acceptance of a request.

17. A computer-implemented method of auto-detection and notification of a medical emergency, comprising:
determining, by one or more computing devices, a user's mobile computing device has entered a healthcare facility at a location defined by a location identifying technology;
sending an alert notification to the user's mobile computing device upon determination that the user's mobile computing device is at an emergency room or healthcare facility;
confirming an emergency event via the user's proactive response or non-response to the alert notification; and
sending notifications to the user's predetermined contacts identified by the user prior to the emergency event to alert the predetermined contacts that the user is in a healthcare facility; and delivering a registration application to a plurality of potential providers authorized to provide patient advocacy, non-medical assistance, provide secondary medical opinions, or other medical or healthcare services; and
storing an online skills catalogue identifying registered individuals or groups and registered types of advocacy, assistance, opinion or other medical or healthcare services.

18. The computer-implemented method of claim 17,
wherein registration of a physician comprises one or more of designation of hospitals to which the physician has admitting privileges, specialties, credentials, and fee structure.

19. The computer-implemented method of claim 17, further comprising:
associating the user with an individual or group to provide services to the user.

20. The computer-implemented method of claim 19,
wherein the association of the user with an individual or group comprises one or more of:
categorization of the services as one or more of requested, in-process, or closed;
identifying in-person patient advocacy services the user wishes to receive;
identifying non-medical services the user wishes to receive; and
identifying user payment information to pay for such services.

21. A computer-implemented method of auto-detection and notification of a medical emergency, comprising:
determining, by one or more computing devices, a user's mobile computing device has entered a healthcare facility at a location defined by a location identifying technology;
sending an alert notification to the user's mobile computing device upon determination that the user's mobile computing device is at an emergency room or healthcare facility;
confirming an emergency event via the user's proactive response or non-response to the alert notification; and
sending notifications to the user's predetermined contacts identified by the user prior to the emergency event to alert the predetermined contacts that the user is in a healthcare facility;
wherein sending notifications to the user or the user's predetermined contacts includes sending information to permit access to documents including one or more of the user's healthcare durable power of attorney, healthcare wishes and directives, medical history, medical summary, allergies, last will and testament, and insurance policy information.

22. The computer-implemented method of claim 21, further comprising:
upon determining the user's mobile computing device has entered a healthcare facility location, initiating a timer; and
when a specified total time from initiation of the timer has elapsed, determining whether the user's mobile computing device remains within the healthcare facility location, and if so, sending the alert to the user's mobile computing device.

* * * * *

UNITED STATES PATENT AND TRADEMARK OFFICE
CERTIFICATE OF CORRECTION

PATENT NO. : 12,160,802 B1
APPLICATION NO. : 17/805538
DATED : December 3, 2024
INVENTOR(S) : Robert M. Deubell Page 1 of 1

It is certified that error appears in the above-identified patent and that said Letters Patent is hereby corrected as shown below:

In the Specification

Column 5, Line 38, delete:
"... user to said question as to whether they are OK is used by ...",
Insert:
--... user to said question as to whether they are OK are used by ...--.

In the Claims

Column 8, Line 16, Claim 2, Line 6, delete:
"... elapsed, redetermining whether the user's mobile com-...",
Insert:
--... elapsed, determining whether the user's mobile com-...--.

Column 8, Line 54, Claim 7, Line 2, delete:
"... wherein the information to permit access the user's health ...",
Insert:
--... wherein the information to permit access to the user's health ...--.

Signed and Sealed this
Twenty-fifth Day of March, 2025

Coke Morgan Stewart
*Acting Director of the United States Patent and Trademark Office*